(12) United States Patent
Kunig et al.

(10) Patent No.: US 6,520,917 B1
(45) Date of Patent: Feb. 18, 2003

(54) METHOD AND APPARATUS FOR MEASURING FUNCTIONALITY OF A PERIODICALLY CHANGING SYSTEM

(75) Inventors: Sabine Vivian Kunig, Saltsburg, PA (US); Horst Erhard Kunig, P.O. Box 192, Saltsburg, PA (US) 15681-0192

(73) Assignee: Horst Erhard Kunig, Saltsburg, PA (US)

( * ) Notice: Subject to any disclaimer, the term of this patent is extended or adjusted under 35 U.S.C. 154(b) by 118 days.

(21) Appl. No.: 09/610,086

(22) Filed: Jul. 1, 2000

Related U.S. Application Data

(63) Continuation-in-part of application No. 08/984,956, filed on Dec. 4, 1997, now abandoned, which is a continuation-in-part of application No. 09/184,606, filed on Nov. 2, 1998, now abandoned.

(51) Int. Cl.[7] .................................................. A61B 5/02
(52) U.S. Cl. ....................................... 600/481; 600/483
(58) Field of Search ................................. 600/300–301, 600/481–486, 500–508, 529, 532, 538; 128/897–898, 920–925

(56) References Cited

U.S. PATENT DOCUMENTS 5,810,011 A * 9/1998 Kunig ........................ 600/481
6,161,038 A * 12/2000 Schookin et al. ........... 600/519

* cited by examiner

*Primary Examiner*—Kevin Shaver
*Assistant Examiner*—Michael Astorino

(57) ABSTRACT

A diagnostic and monitoring device is disclosed to determine functionality of the cardiocirculatory system, to generate a cardiocirculatory performance scale for display in a performance diagram, and to measure cardiocirculatory functionality on the performance scale. The diagnostic and monitoring device further identifies zones of criticalities on the performance scale used as reference to diagnose myocardial fitness, myocardial impairment, dysfunctions, critical illness, improvement and/or deterioration of cardiocirculatory status, and outcome. The method and device have utility to design and monitor therapies for differential treatment of myocardial impairment, dysfunctions, rehabilitation, and conditioning exercises, to evaluate the efficacy of drugs, and to predict outcome of interventions.

20 Claims, 6 Drawing Sheets

Relationship of
Separation $|m_1 - m_2| > em_1 + em_2$

METHOD AND APPARATUS FOR MEASURING FUNCTIONALITY OF A PERIODICALLY CHANGING SYSTEM

CROSS REFERENCE TO RELATED APPLICATION

This application is a continuation-in-part of application Ser. No. 08/984,956, filed on Dec. 4, 1997 abandoned and a further continuation-in-part of application Ser. No. 09/184,606, filed Nov. 2, 1998 abandoned.

FIELD OF THE INVENTION

The present invention relates to the functionality of a system periodically changing in time and, more specifically, to a method and apparatus for establishing a performance scale for determining functionality of the system on the performance scale.

DESCRIPTION OF PRIOR ART

For the cardiocirculatory system functionality is usually inferred by relating maximal or minimal values of the periodically changing hemodynamic parameters during one cycle to an empirically derived surrogate range of normalcy. The empiricism associated with the surrogate range of normalcy provides for ambiguous patient diagnosis. Absent is a cardiocirculatory performance scale descriptive of the functionality of the cardiocirculatory system to measure objectively and quantitatively human performance.

Disclosed in U.S. Pat. No. 5,370,122 is a method to establish the synergy of several hemodynamic parameters from which to deduce functionality. Also, U.S. Pat. No. 5,810,011 discloses a method to measure the synergy of several different parameters to deduce functionality for display in a single reference frame. Both disclosures fail to describe functionality with specificity on a performance scale.

It is therefore an object of the present invention to provide a cardiocirculatory performance scale for hemodynamic parameters to measure human performance on said scale and to display functionality in a performance diagram.

It is a further objective of the present invention to identify basal units on the performance scale for hemodynamic parameters to allow measurements of hemodynamic parameters in basal units for display in a performance diagram.

It is still another object of the present invention to determine zones of criticalities for sustenance of life, myocardial impairment, myocardial fitness, dysfunctions from the human performance scale for diagnosis of cardiocirculatory compliance and failure, for improvement and/or deterioration of cardiocirculatory status, and for design and monitoring therapeutic interventions.

SUMMARY OF THE PRESENT INVENTION

According to the present invention, there is provided a diagnostic device and method for diagnosis of the functionality of the cardiocirculatory system of an individual, measured on a performance scale, and displayed in a performance diagram said scale and performance diagram to be used for diagnosis of myocardial fitness, myocardial impairment, dysfunctions, critical illness, cardiocirculatory compliance, cardiocirculatory failure, improvement and/or deterioration of cardiocirculatory status, and outcome. The device includes the combination of sensors responsive to physiological parameters of an individual changing in time, collectively referred to as A, at an initial time $t_1$, denoted, $A_1$ and at a subsequent time $t_2$, denoted $A_2$, means to transmit A to a computer for computing the magnitudes of A at various times, the difference of the magnitudes of A at various times, the ratio of the change of A at various times in relation to the magnitude of A at an initial time, and the time trend of the computed parameters. The computer further includes sensors responsive to pre-selected magnitudes of A which are fractions or multiples determined from a standard signal A under standard conditions to serve as basal unit, on a cardiocirculatory performance scale and to establish zones of criticalities. Still further, the computer includes means for comparing the measured signal A with its standard to produce a signal A* which expresses signal A in basal units on the cardiocirculatory performance scale for determining functionality, said functionality comprising myocardial fitness, myocardial impairment, dysfunctions, critical illness, cardiocirculatory compliance, cardiocirculatory failure, improvement and/or deterioration of cardiocirculatory status, and, outcome, where said diagnosis is derived by reference to the zones of criticalities and the time trend of the computed parameters. The device further provides means for selecting therapeutic interventions, depending on the attainment of zones of criticalities, displays and monitors for recording improvement or deterioration by departing or approaching the zones of criticalities, recording means, audible and visible warning means activated upon the establishment of pre-selected values to warn of criticalities, and modems for transmission to a central storage facility.

BRIEF DESCRIPTION OF THE DRAWINGS

The present invention will be more fully understood when the following detailed description is read in conjunction with the accompanying drawings in which.

DETAILED DESCRIPTION OF THE PREFERRED EMBODIMENT

Figure 1:
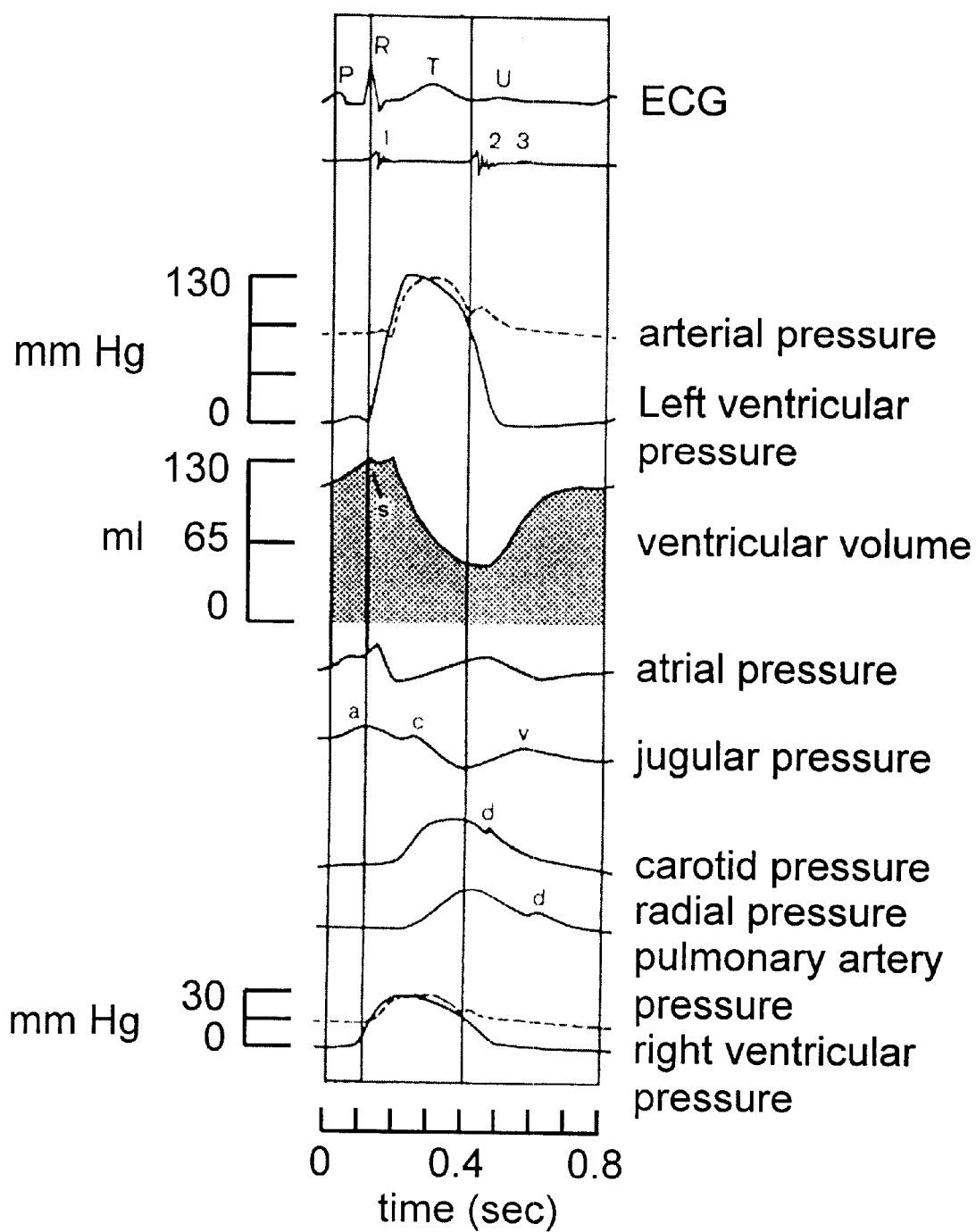
FIG. 1 illustrates the time sequence of physiological parameters A, said parameters A to include electrocardiographic signals, ECG, arterial pressure, left ventricular pressure, atrial pressure, jugular pressure, carotid pressure, radial pressure, pulmonary artery pressure, right ventricular pressure, and ventricular volume, collectively referred to as signals A, in the instant invention during the time of one heart beat.

Referring now to FIG. 1, there are displayed electromechanical physiological signals A as a function of time. The magnitudes of the electromechanical signals at a specific time describe the state of the system at that time but not functionality. Sustenance of life, for example, reflects functionality. For life to be sustained a minimal difference of A at two different times is needed. To determine functionality of the cardiocirculatory system the difference of A at two different times, AA, is derived as $$AA = A_1 - A_2 \quad (1)$$

Expanding the right side of equation (1) by the ratio of $A_1/A_1$ yields $$AA = (A_1 - A_2) \times \frac{A_1}{A_1} = EF(A) \times A_1 \quad (2)$$

where EF(A) is the ejection fraction of A, describing the efficiency of the cardiocirculatory system.

$$EF(A) = (A_1 - A_2)/A_1 \quad (3)$$

Physiological parameters change with body surface area, BSA, and age. Further, the instantaneous demand placed upon the cardiocirculatory system is not only met by the magnitude of AA but also by the adjustment of the time of one heart beat, RR, (R to R interval in the electrocardiogram) during which AA is expended.

To standardize with respect to BSA and to convert a per-beat event into a per-unit time event equations (1) and (2) are divided by BSA and RR to yield the functionality equations $$AA^* = A_1^* - A_2^* \quad (4)$$

$$AA^* = EF(A) \times A_1^* \quad (5)$$

where $AA^* = AA/(BSA \times RR)$ $A_1^* = A_1/(BSA \times RR)$ and $A_2^* = A_2/(BSA \times RR)$ To establish a cardiocirculatory performance scale, valid for all subjects, a basal AA*, denoted $AA^*_{basal}$, is required, which has assigned a basal unit, 1 BU. $AA^*_{basal} = 1$ BU. In general, basal units are derived as a fraction of a constant property. For example, the original basal unit of measuring a length is one meter, which is derived as a fraction of the constant property of the earth circumference around the equator. Hemodynamic parameters change with age due to physiological processes. Such physiological process include growth during childhood which is completed approximately at age of 20 years and aging which commences approximately at age of 30 years. The hemodynamic parameters of the age group of 20 to 30 years, measured at rest in supine position is a constant property for all subjects unaffected by growth and aging. Therefore, they have utility for use as basal units for adults on the cardiocirculatory performance scale.

To determine the basal value, $AA^*_{basal}$, needed to sustain life, hemodynamic values for subjects of the age group of 20 to 30 years measured in supine position under resting conditions are inserted into equation (4). To convert electromechanical physiological parameters AA, measured in conventional units into the same parameters measured in basal units AA is divided by BSA, RR, and $AA^*_{basal}$, according to $$AA*(BU) = \frac{AA \text{ (conventional units)}}{BSA(m^2) \times RR(\sec) \times AA^*_{basal} \text{ (conventional units)}} \quad (6)$$

Further, a basal value of EF(A), denoted $EF(A)_{basal}$, is derived from equation (3) by insertion of hemodynamic parameters for subjects of the 20 to 30 years age group. Subsequent substitution of EF(A)basal into equation (5) yields $A_1^*_{basal}$ as $AA^*_{basal}/EF(A)_{basal}$ or $1/EF(A)_{basal}$ Additionally, $A_2^*_{basal}$ is derived from equation (4) as $A_2^*_{basal} = A_1^*_{basal} - AA^*_{basal} = A_1^*_{basal} - 1$.

Figure 2:
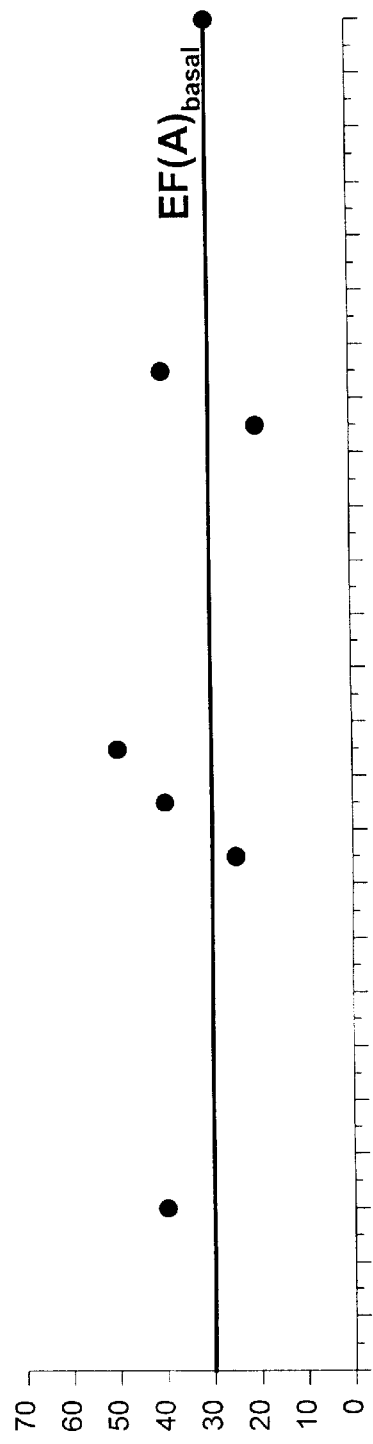
FIG. 2 illustrates a performance diagram used to determine functionality of the cardiocirculatory system and to diagnose myocardial impairment, myocardial fitness, dysfunctions, critical illness, cardiocirculatory compliance, cardiocirculatory failure, improvement and/or deterioration of cardiocirculatory be status, and outcome.
Figure 2:

Referring now to FIG. 2, there is shown a performance diagram, according to the teachings of the instant invention. A computer computes AA*, $A_1^*$, $A_2^*$, and EF(A) from the functionality equations (3), (4), and (5) and plots AA*, $A_1^*$, and $A_2^*$ on a lower scale versus time and EF(A) on an upper scale also versus time. The upper plot shows the efficiency with which $A_1^*$ of the lower plot is converted to AA*, according to equation (5). The lower plot illustrates the manner in which a specific AA* is derived in a transition from $A_1^*$ to $A_2^*$, according to equation (4).

Basal values, $EF(A)_{basal}$, $A_1^*_{basal}$, $AA^*_{basal}$, and $A_2^*_{basal}$ are added to the performance diagram of FIG. 2 as horizontal lines. The basal lines serve to delineate zones of criticalities. With reference to the basal lines a performance diagram determines cardiocirculatory status as:

1. compliant, when all parameters fall into a zone, where they equal or exceed basal values,
2. failing (without immediate danger of death), when at least one parameter EF(A), $A_1^*$, or $A_2^*$ falls into a zone so as to not equal or exceed basal values,
3. critical illness (failure with immediate danger of death) when AA* falls into a zone, given by $AA^* < AA^*_{basal}$. Critical illness may occur as a result of inefficient operation (myocardial impairment), when EF(A) is sufficiently small to cause $AA^* < AA^*_{basal}$ or as a result of circulatory dysfunction, when $A_1^*$ is sufficiently small to cause $AA^* < AA^*_{basal}$, according to equation 5,
4. deterioration of cardiocirculatory status, when the trend of two successive measurements of at least one parameter departs from the basal value,
5. improvement of cardiocirculatory status, when the trend of two successive measurements of all parameters returns to basal value.

All values EF(A), $A_1^*$, AA*, $A_2^*$ are expressed in BUs for use in the performance diagram. Basal values, according to the instant invention, serve to define the zones of critical illness, myocardial impairment, myocardial fitness, dysfunctions, cardiocirculatory compliance, cardiocirculatory failure, improvement, and/or deterioration of cardiocirculatory status. Expressing these parameters in terms of BUs permits a quantitative determination of the intensity of myocardial impairment, myocardial fitness, dysfunctions, and critical illness. By measuring performance on the cardiocirculatory performance scale the instant invention teaches the assessment of general age related diseases and the specific dysfunctions which may occur at any age.

The performance diagram, measured at rest, permits the determination of improvement and/or deterioration and, thus, outcome from trend measurements. Trends departing from the basal lines indicate deterioration and trends approaching basal values indicate improvement. The performance diagram, established from measurements not measured at rest, reflects the stress of physical activities. The concomitant changes of EF(A), $A_1^*$, AA*, and $A_2^*$ of the compliant cardiocirculatory system of an exercising subject are a measure of physical fitness.

To establish a trend for determination of progress and/or regress successive measurements must be truly different from each other. All measurements are afflicted with an unavoidable error. The true value of the measurement is never known only that it falls within the error range. For two measurements to be truly different the error ranges cannot overlap otherwise both measurements may fall into the overlap region where they would not be different from each other.

Figure 3:
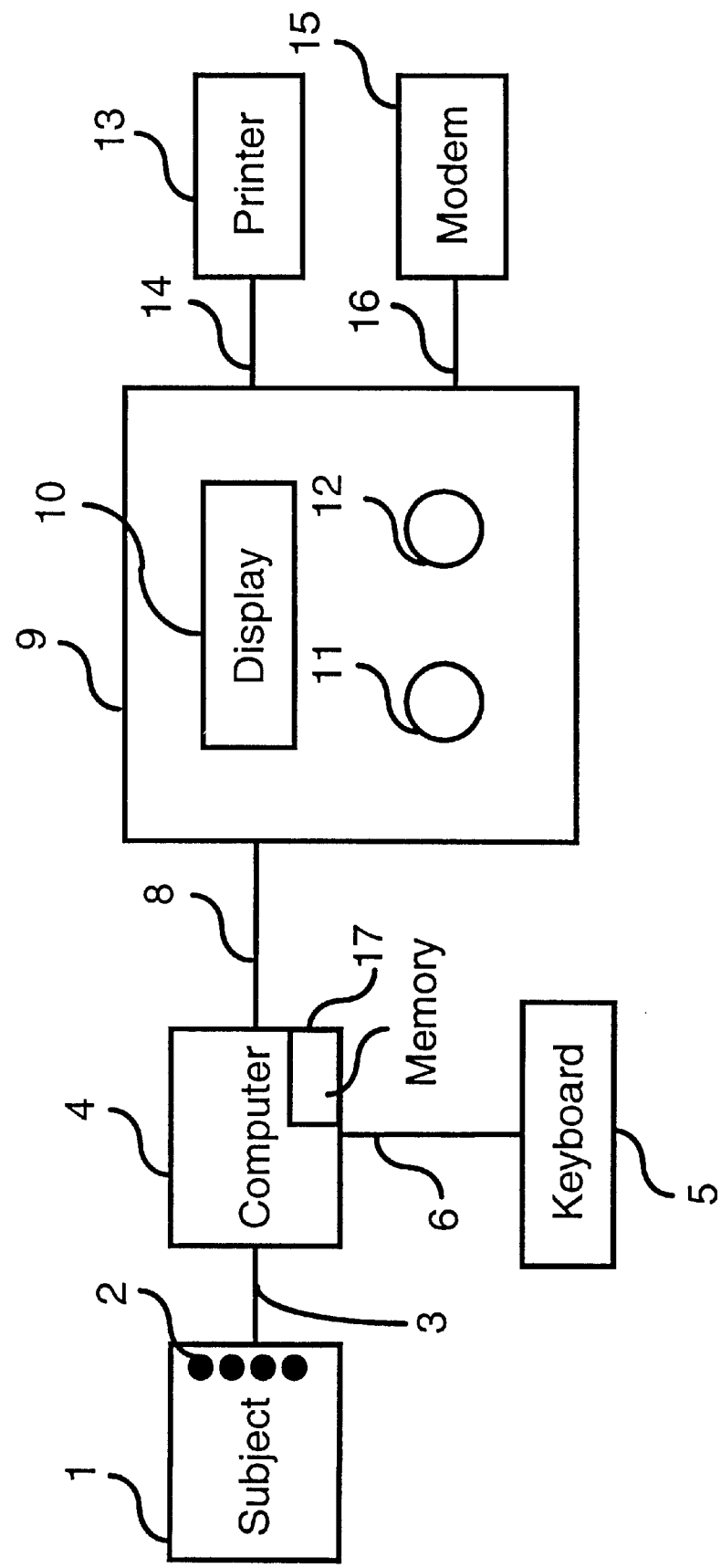
FIG. 3 shows a block diagram of the apparatus to practice the instant invention.

The embodiment, as shown in FIG. 3 illustrates the teachings of the instant invention. Accordingly, sensors 2 are placed on a subject 1 to detect signals representative of physiological signals A to include but not limited to mechanical signals, ventricular volumes, atrial volumes, cross-sectional ventricular areas, cross-sectional atrial areas, ventricular pressures, arterial pressures, central venous pressure, jugular pressure, radial pressure, pulmonary artery pressure, carotid pressure, atrial pressure, echocardiographic signals, ultra-sound signals, bioimpedance signals, electrical signals, electrocardiographic signals, magnetic signals, chemical signals, arterial oxygen concentration, venous oxygen concentration, oxygen consumption, temperature signals, time signals, heart rate, and combinations thereof which are transmitted on multi-line wire 3 to computer 4. Such sensors 2 may include catheters, electrodes, electrocardiographs, bioimpedance measuring equipment magnetic resonance measuring equipment, ultra-sound equipment, pressure transducers, pressure cuffs, temperature sensors, chemical sensors, time sensors, and echocardiographic sensors. Additional input representative of patient information including weight, height, body surface area, pre-selected time intervals, and pre-selected basal electromechanical physiological parameters values. is provided from a keyboard 5 to computer 4 on line 6. Computer 4 is programmed to process the incoming signals on line 6 to establish a basal value for $AA^*_{basal}$ as basal unit for the cardiocirculatory functionality scale and to establish basal values EF(A)basal, $A_1^*{}_{basal}$, and $A_2^*{}_{basal}$ for further establishing zones of criticality. Computer 4 is also programmed to process the it incoming signals on line 3, to determine their magnitudes and to convert them into multiples of the basal unit for use on the cardiocirculatory performance scale. Further, computer 4 generates a performance diagram, establishes zones of criticality and determines myocardial impairment, myocardial fitness, dysfunctions, and critical illness by reference to the zones of criticality. Additionally, computer 4 determines suitable values of EF(A), AA*, $A_1^*$, and $A_2^*$ to establish a trend for diagnosis of improvement and/or deterioration of the cardiocirculatory system. All parameters, representative of said functionality, are transmitted by line 8 to a monitor 9 which is comprised of a display 10, audible and visual alarms 11 to warn of emergencies if preset values of the parameters are attained, and indicators 12 to display diagnosis of myocardial impairment, myocardial fitness dysfunctions, critical illness, compliance, failure, improvement, deterioration, outcome, and physical fitness from the attainment of specific magnitudes of the electromechanical physiological variables, measured on the cardiocirculatory performance scale by reference to the zones of criticalities. The signals displayed by display 10 and the audio and visual alarms 11 and the signals displayed by indicator 12 are transmitted on line 14 to a printer 13 for producing hard copies and on line 16 to a modem 15 for in transmission to central storage and retrieval. A memory 17 in the computer 4 serves as storage of all information and data.

Figure 4:
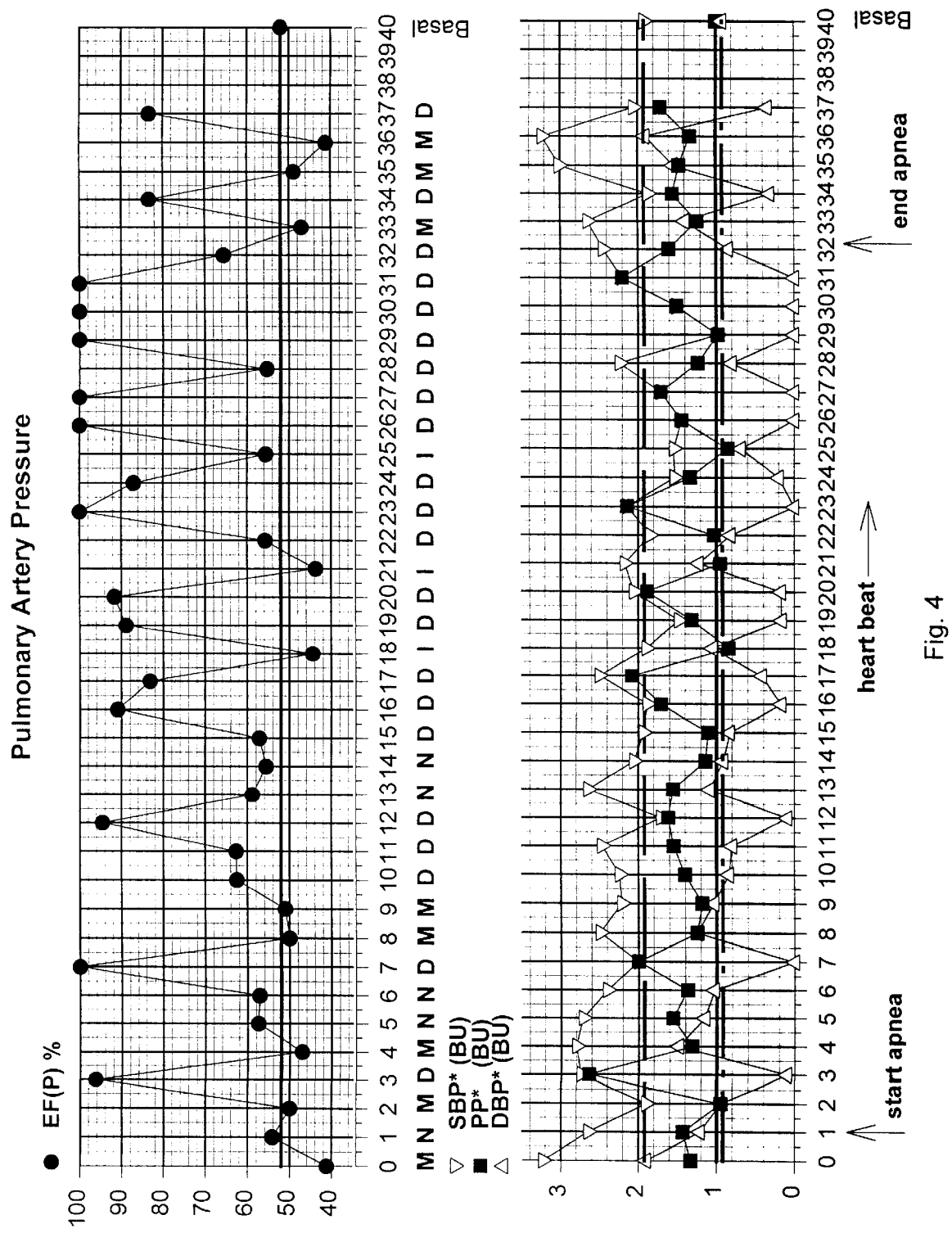
FIG. 4 illustrates the utility of the present invention to determine cardiocirculatory functionality and to diagnose myocardial impairment, myocardial fitness, dysfunctions, critical illness, cardiocirculatory compliance, cardiocirculatory failure, improvement and/or deterioration of cardiocirculatory status, and outcome of a patient.

Referring now to FIG. 4, there is shown a performance diagram generated by computer 4 of FIG. 3 from data published by it Bonignore et.al. in an article entitled, Obstructive sleep apneas, in Respiratory Critical Care Medicine 1994;149:155–159, prior to, during and after termination of a sleep apnea. Here the physiological parameter AA* is the pulmonary artery pulse pressure, PP*, $A_1^*$ is the systolic pulmonary artery pressure SBP*, and $A_2^*$ is the diastolic pulmonary artery pressure, DBP* all measured in basal units and displayed versus time at successive heart beats, according to the instant invention, said performance diagram showing a compliant system, C, alternating with a failing system and more specifically showing a myocardially impaired system, M, a dysfunctional system, D, and a critically ill system, I, during the apneic period. According to the instant invention, an alarm is triggered upon the attainment of the danger zones of myocardial impairment and dysfunctions. A different sound may be triggered upon the attainment of the zone of critical illness, thus, providing an instant warning of imminent death.

Figure 5:
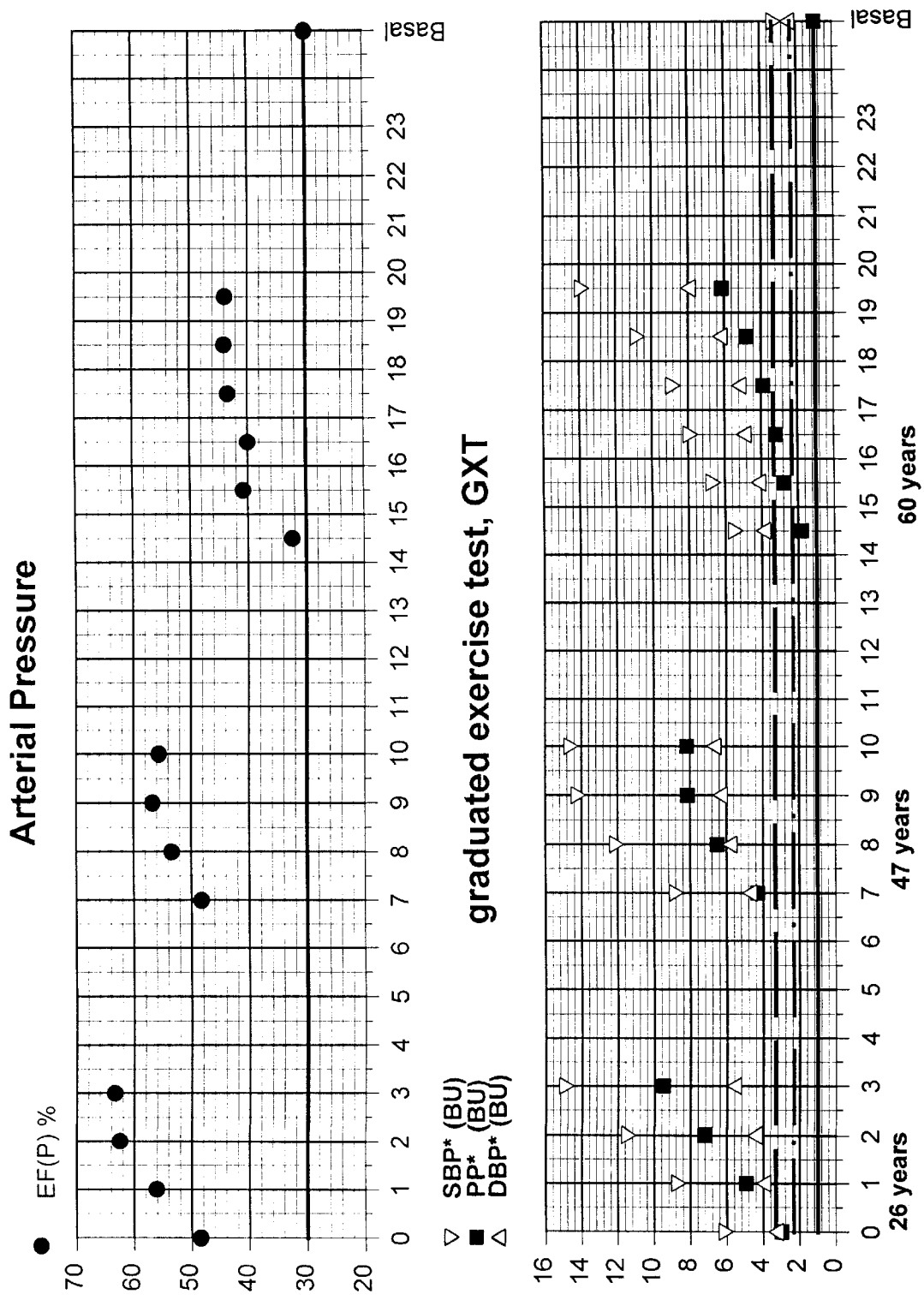
FIG. 5 demonstrates the utility of the present invention to diagnose cardiocirculatory fitness.

Referring now to FIG. 5, there is shown a performance diagram generated by computer 4 of FIG. 3 from data published by R. A. Wolthuis et. al. in an article entitled, The response of healthy men to treadmill exercise, Circulation 1977;55:153–157. Here the electromechanical parameter AA* is the arterial pulse pressure, $A_1^*$ is the systolic arterial blood pressure, and $A_2^*$ is the diastolic arterial blood pressure. The performance diagram of FIG. 5 examines subjects of the three age groups of 26 years, 47 years and 60 years performing a graduated exercise test, GXT. According to the instant invention, the performance diagram reveals diminishing efficiency of the cardiocirculatory system with increasing age. It permits assessment of cardiocirculatory performance, design and monitoring of rehabilitation and conditioning exercise programs.

Figure 6:
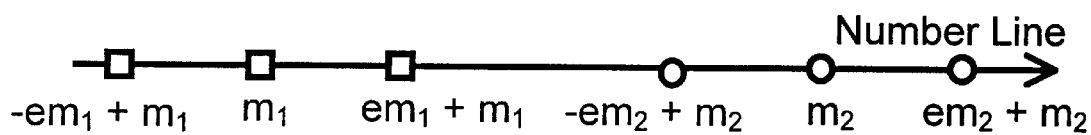
FIG. 6 illustrates the utility of the relation of separation of subsequent measurements to assure accurate trend determination for improvement and/or deterioration diagnosis.

Referring now to FIG. 6, there is shown the relationship of separation for two measurements from each other which is a requirement for accurate trend determination from which to diagnose improvement and/or deterioration. All measurements are afflicted with errors. The true value of a measurement is never known, only that it lies within the error range of the measurement. Placing two measurements $m_1$ and $m_2$ and their respective error ranges$\pm e$ $m_1$ and$\pm e$ $m_2$ on a number line reveals the two measurements to be truly different when the error ranges of both measurements do not overlap. Otherwise both measurements $m_1$ and $m_2$ may fall into the overlapping region where they would not be different from each other. The condition for two measurements to be different can be expressed by the relationship age of separation $$|m_1-m_2|>e\ m_1+e\ m_2 \qquad (7)$$

where $|m_1-m_2|$ is the absolute value of the difference of ml and $m_2$. Computer 4 in FIG. 3 selects measurements for trend determination to diagnose cardiocirculatory compliance and failure from all measurements satisfying the relationship of separation.

In other embodiments of the present invention other physiological parameters including but not limited to mechanical signals, ventricular volumes, atrial volumes, cross-sectional ventricular areas, cross-sectional-atrial areas, ventricular pressures, arterial pressures, central venous pressure, jugular pressure, radial pressure, pulmonary artery pressure, carotid pressure, atrial pressure, echocardiographic signals, ultra-sound signals, bioimpedance signals, electrical signals, electrocardiographic signals, magnetic signals, chemical signals, arterial oxygen concentration, venous oxygen concentration, oxygen consumption, temperature signals, time signals, heart rate, and combinations thereof, including but not limited to ventricular, atrial, aortic energies, and work, together with other constant physiological parameters to serve as basal units, said parameters to be used to determine functionality from which to select therapeutic interventions and to monitor improvement and/or deterioration, and to evaluate drugs.

While the present invention has been described in connection with the preferred embodiments of the various figures, it is to be understood that other similar embodiments may be used or modifications and additions may be made to the described embodiment for performing the same functions of the present invention without deviating therefrom. Therefore, the present invention should not be limited to any single embodiment, but rather construed in breadth and scope in accordance with the recitation of the appended claims.

We claim:

1. A cardiac diagnostic device for establishing cardiocirculatory functionality of an individual consisting of:
    means responsive for measuring physiological parameters of a subject;
    means responsive to the measurements of physiological parameters;
    means for providing cardiocirculatory functionality equations;
    means for computing to derive cardiocirculatory functionality from measured physiological, Parameters and cardiocirculatory functionality equations;
    means for deriving a cardiocirculatory performance scale;
    means for establishing zones of criticality on the cardiocirculatory performance scale:
    means for measuring cardiocirculatory functionality on the cardiocirculatory performance scale;
    means for display cardiocirculatory functionality in a cardiocirculatory performance diagram,
    means for providing the relation for separation, and
    means responsive to the relation of separation to determine the values of two subsequent measurements to be different and allowing only said different measurements to be processed further.

2. The cardiac diagnostic device according to claim 1 wherein said measurements of physiological parameters include.

3. The cardiac diagnostic device according to claim 1 wherein said means for deriving said cardiocirculatory performance scale includes a computer for establishing baa units for said cardiocirculatory performance scale front inputs of multiples of constant physiological parameters via a keyboard, said basal units are used to further establish zones of criticality.

4. The cardiac diagnostic device according to claim 3 wherein said means for establishing cardiocirculatory functionality includes said computer for determining cardiocirculatory functionality from the functionality equations $$AA^* = EF(A) \times A_1^*$$

$$AA^* = A_1^* - A_2^*$$

$$EF(A) = (A_1 - A_2)/A_1$$

wherein $AA^*$, $A_1^*$, and $A_2^*$ equal $AA$, $A_1$, and $A_2$ referenced to time, body surface area and basal $AA^*$ and wherein $A_1$ is a physiological parameter, measured at time $t_1$, $A_2$ is a physiological parameter, measured at time $t_2$, and $AA$ is the difference of $A_{1\ and\ A2}$.

5. The cardiac diagnostic device according to claim 4 wherein said computer measures cardiocirculatory functionality on the cardiocirculatory performance scale in multiples of basal units for display in a cardiocirculatory performance diagram, and further establishes a trend of said functionality.

6. The cardiac diagnostic device according to claim 5 wherein said computer diagnoses myocardial impairment, myocardial fitness, dysfunctions, critical illness, cardiocirculatory compliance, cardiocirculatory failure, improvement of cardiocirculatory status, and deterioration of cardiocirculatory status by comparison of $EF(A)$, $AA^*$, $A_1^*$, $A_2^*$, with the zones of criticality and the zones of criticality time trend;
    wherein $EF(A)$ greater than the basal unit establishes the zone of myocardial fitness;
    wherein $EF(A)$ less than the basal unit establishes the zone of cardiocirculatory failure due myocardial impairment;
    wherein $A_1^*$ less than the basal unit establishes the zone of cardiocirculatory failure due to cardiocirculatory dysfunctions;
    wherein $Fe_2^*$ less than the basal unit establishes the zone of cardiocirculatory failure due to cardiocirculatory dysfunctions;
    wherein $AA^*$ less than the basal unit establishes a zone of cardiocirculatory failure, more specifically of critical illness;
    wherein trends of $EF(A)$, $A_1^*$, $AA^*$, and $A_2^*$ approaching basal units denote improvement;
    wherein trends of $EF(A)$, $A_1$, $AA^*$, and $A_2^*$ departing from the basal units denote deterioration.

7. The cardiac diagnostic device according to claim 6 wherein said computer system provides the relation of separation $$|m_1 - m_2| > e\ m_1 + e\ m_2$$

and where said computer system determines measurement $m_1$ and $m_2$ of physiological parameters A and physiological parameters A derivatives to be different when the relation of separation is satisfied and wherein said computer system allows for processing only different physiological parameters A and different derivations of physiological parameters A.

8. The cardiac diagnostic device according to claim 6 to design and monitor patient-specific therapies for myocardial impairment, myocardial fitness, dysfunctions, critical illness, cardiocirculatory compliance, cardiocirculatory failure, improvement of cardiocirculatory status, and deterioration of cardiocirculatory status.

9. The cardiac diagnostic device according to claim 6 to diagnose cardiocirculatory fitness and to design and monitor patient-specific rehabilitation and subject-specific conditioning programs.

10. The cardiac diagnostic device of claim 6 wherein said computer evaluates the efficacy of drugs to effectuate patients in the zones of criticality.

11. The cardiac diagnostic device according to claim 1 wherein said physiological parameters include mechanical signals, ventricular volumes, atrial volumes, cross-sectional ventricular areas, cross-sectional atrial areas, ventricular pressures, arterial pressures, central venous pressure, jugular pressure, radial pressure, pulmonary artery pressure, carotid pressure, atrial pressure, echocardiographic signals, ultrasound signals, bioimpedance signals, electrical signals, electrocardiographic. signals, magnetic signals, chemical signals, arterial oxygen concentration, venous oxygen concentration, oxygen consumption, temperature signals, time signals, heart rate, and combinations thereof.

12. The cardiac diagnostic device of claim 6 wherein said means responsive to the measurement of said physiological signals include catheters, electrodes, electrocardiographs, bioimpedance measuring equipment magnetic resonance measuring equipment, ultra-sound equipment, pressure transducers, pressure cuffs, temperature sensors, chemical sensors, time sensors, and echocardiographic sensors.

13. The cardiac diagnostic device according to claim 6 for determining outcome by reference to zones of criticality.

14. A method of diagnosing cardiocirculatory functionality of an individual; said method including the steps of:
measuring physiological parameters A of said individual at an initial time $t_1$, denoted $A_1$, and at a subsequent time $t_2$, denoted $A_2$;
establishing cardiocirculatory functionality from the functionality equations $$AA^* \ EF(A) \times A_1$$

$$AA^* = A_1^* - A_2^*$$

$$EF(A) = (A_1 - A_2)/A_1$$

wherein $AA^*$, $A_1^*$, and $A_2^*$ equal $AA$, $A_1$, and $A_2$ referenced to time, body surface area, and basal $AA^*$;
establishing a cardiocirculatory performance scale;
establishing basal units on the cardiocirculatory performance scale;
referencing physiological measured data in terms of the basal unit and display of said referenced data on the cardiocirculatory performance scale;
establishing a performance diagram for display of $EF(A)$ and data placed on the cardiocirculatory performance scale;
establishing zones of criticality by reference to the basal units $EF(A)_{basal}$, $A_1^*{}_{basal}$, $A_2^*{}_{basal}$, and $AA^*{}_{basal}$;
diagnosing myocardial fitness in the zone $EF() > EF(A)_{basal}$;
diagnosing myocardial impairment in the zone $EF(A) < EF(A)_{basal}$;
diagnosing cardiocirculatory dysfunctions in the zone $A_1^* < A_1^*{}_{basal}$;
diagnosing cardiocirculatory dysfunction in the zone $A_2^* < A_2^*{}_{basal}$;
diagnosing critical illness in the zone $AA^* < AA^*{}_{basal}$;
diagnosing deterioration of cardiocirculatory status, when the trend of two successive measurements departs from the basal unit;
diagnosing improvement of cardiocirculatory status, when the trend of two successive measurements returns to the basal unit; and
subjecting the measurements of physiological parameters and their derivations to the test of separation, according to the relationship $$|m_1 - m_2| > e \ m_2 + e \ m_2.$$

15. The method of claim 14 including the steps of design and monitoring of patient-specific rehabilitation programs for treatment of dysfunctionalities, myocardial impairment, critical illness, and effectuating cardiocirculatory compliance, cardiocirculatory failure, improvement of cardiocirculatory status, and deterioration of cardiocirculatory status.

16. The method of claim 14 including the steps of design and monitoring subject-specific conditioning programs.

17. The method of claim 14 including the steps of evaluating the efficacy of drugs by reference to the zones of criticality and the trend of the parameters computed from the functionality equations.

18. The method of claim 14 including the steps of determining outcome of an intervention by reference to functionality and the time trends thereof.

19. The method of claim 14 wherein said step of measuring includes physiological parameters changing in time, include mechanical signals, ventricular volumes atrial volumes, cross-sectional ventricular areas, cross-sectional atrial areas, ventricular pressures, arterial pressures, central venous pressure, jugular pressure, radial pressure, pulmonary artery pressure, carotid pressure, atrial pressure, echocardiographic signals, ultra-sound signals, bioimpedance signals, electrical signals, electrocardiographic signals, magnetic signals, chemical signals, arterial oxygen concentration, venous oxygen concentration, oxygen consumption, temperature signals, time signals, heart rate, and combinations thereof.

20. The method of claim 14 wherein said means responsive to the measurement of said physiological signals include catheters, electrodes, electrocardiographs, bioimpedance measuring equipment magnetic resonance measuring equipment, ultra-sound equipment, pressure transducers, pressure cuffs, temperature sensors, chemical sensors, time sensors, and echocardiographic sensors.

* * * * *